United States Patent [19]
Liddell

[11] Patent Number: 5,894,062
[45] Date of Patent: Apr. 13, 1999

[54] PROCESS FOR THE RECOVERY OF POLYHYDROXYALKANOIC ACID

[75] Inventor: John MacDonald Liddell, Stockton on Tees, United Kingdom

[73] Assignee: Monsanto Company, St. Louis, Mich.

[21] Appl. No.: 08/793,832

[22] PCT Filed: Aug. 15, 1995

[86] PCT No.: PCT/GB95/01926

§ 371 Date: Jun. 16, 1997

§ 102(e) Date: Jun. 16, 1997

[87] PCT Pub. No.: WO96/06179

PCT Pub. Date: Feb. 29, 1996

[30] Foreign Application Priority Data

Aug. 18, 1994 [GB] United Kingdom ............... 9416690

[51] Int. Cl.⁶ .................. C12P 7/62; C12P 7/42
[52] U.S. Cl. ............ 435/135; 435/136; 435/146; 435/259; 435/267; 435/829; 435/874; 528/354; 528/358; 528/361; 560/185
[58] Field of Search ................... 435/135, 136, 435/146, 267, 259, 829, 874; 560/185; 528/358, 361, 354

[56] References Cited

U.S. PATENT DOCUMENTS

| | | | |
|---|---|---|---|
| 4,968,611 | 11/1990 | Traussig et al. | 435/135 |
| 5,110,980 | 5/1992 | Ramsay et al. | 435/146 |
| 5,213,976 | 5/1993 | Blauhut et al. | 435/135 |
| 5,266,422 | 11/1993 | Reusch et al. | 429/192 |
| 5,268,422 | 12/1993 | Yalpani | 528/354 |
| 5,302,525 | 4/1994 | Groleau et al. | 435/136 |
| 5,395,919 | 3/1995 | Lee et al. | 435/135 |
| 5,434,062 | 7/1995 | Groleau et al. | 435/135 |

FOREIGN PATENT DOCUMENTS

| | | |
|---|---|---|
| 0 124 309 | 11/1984 | European Pat. Off. . |
| 0 355 307 | 2/1990 | European Pat. Off. . |
| 2 338 291 | 8/1977 | France . |
| WO 93/11656 | 6/1993 | WIPO . |

*Primary Examiner*—Herbert J. Lilling
*Attorney, Agent, or Firm*—Gary M. Bond; Arnold, White & Durkee

[57] ABSTRACT

A hydroxyalkanoic acid (PHA) is recovered from matter derived from living organisms by dissolving the PHA in a solvent which is a lower ketone, dialkyl ether or a lower alcohol or a monocarboxylic acid ester thereof, separating the solution from such matter and recovering PHA from the solution.

12 Claims, No Drawings

PROCESS FOR THE RECOVERY OF POLYHYDROXYALKANOIC ACID

THIS INVENTION relates to a process for the recovery of polyhydroxyalkanoic acid.

It has been found that it is possible to produce polyhydroxyalkanoic acid for example polyhydroxybutyric acid in microorganisms, for example Alcaligenes and in plants. The recovery of the polymer, especially from plants in a state of sufficient purity for it to be useable as a plastics material presents difficulties however. Matter derived from plants for example seeds and fruits is herein referred to as vegetable matter.

Surprisingly we have found that it is possible to carry out an effective separation of polyhydroxy-alkanoic acid from matter derived from organisms which contains it by dissolving the polyhydroxyalkanoic acid (PHA) in a solvent which is a lower ketone, dialkyl ether or a lower alcohol or an ester thereof, separating the solution so formed from undissolved matter and recovering PHA from the solution.

The invention therefore comprises a process in which a polymer of a hydroxyalkanoic acid (PHA)is recovered from matter derived from living organisms which comprises dissolving the PHA in a solvent which is a lower ketone, dialkyl ether, a lower alcohol or an ester thereof, separating the solution from such matter and recovering PHA from the solution.

The process is very suitable for the recovery of polymers and copolymers of hydroxybutyric acid for example a polymer of hydroxybutyric and hydroxyvaleric acids.

It is often desirable to crush or mill the vegetable matter prior to contacting it with the solvent in order to permit more intimate contact of the solution with the PHA.

If the solvent is miscible with water it is preferred that the PHA be precipitated from the solution by adding water. Solvents which are immiscible with water may also be used in which case the PHA may be recovered by evaporating the solvent or by temperature cycling by which the PHA is dissolved at a high temperature and the solution cooled to precipitate PHA. The solvent may in the latter case be reused for further extraction of PHA but it is desirable if this is done to replace at least part of the solvent by fresh solvent so as to prevent undue build up of impurities on continued recycle of the solvent. Fresh solvent may be produced by distilling pure solvent from used impure solvent.

Preferred water miscible solvents include lower ketones, especially acetone and lower alcohols for example methanol, ethanol, or a propanol which is suitably isopropanol. Such solvents may be used in the presence or absence of water. For example ethanol/water mixtures may be used which can be but are not limited to azeotropic compositions.

If the vegetable matter contains oil it is preferred that the oil be extracted from the vegetable matter before it is treated according to this invention. This may be done by pressing the vegetable matter to expel oil and/or by extracting it with a water immiscible solvent which is suitably a paraffin or cyclo-paraffin containing for example 4 to and preferably 5 to 8 carbon atoms. The water immiscible solvent is preferably one which does not dissolve substantial quantities of PHA.

If desired oil and PHA may be extracted together from vegetable matter by dissolving them in a solvent, separating the solids from undissolved vegetable matter and separating the PHA from the solution, for example by cooling to precipitate it or adding a liquid which reduces its solubility in the solvent, for example water.

The solvent extraction is preferably carried out at a temperature above 100° C. and preferably above 120° C. It is however preferred that the temperature should not substantially exceed 150° C. in order to avoid depolymerisation of the PHA. Suitably a ratio of 1.5:1 to 10:1 of solvent (ml) to solid (grams) should be used so as to secure easy handling of the mixture of vegetable matter and solvent and effective recovery of PHA. PHA may be recovered by cooling the solution for example to 20–80° C. and preferably 30 to 50°, or by evaporating the solvent. If a water miscible solvent is employed the solution may be cooled to below 100° C. for example to a temperature in the range 40 to 90 and water added for example 10 to 50% and preferably 25 to 35% by volume to the solution to cause precipitation. In general the higher the molecular weight of the monomer units in the PHA the lower the temperatures necessary to carry out the solution step. Among solvents of low water miscibility which may be used are included the higher alcohols for example $C_4$ to $C_{10}$ alcohols, for example butanol, and amyl alcohol esters containing $C_4$ to $C_{10}$ carbon atoms for example ethyl acetate and amyl acetate and higher ketones for example cyclo hexanone, and methyl isobutyl ketone.

Based on the Hildebrand expression for the square root of the cohesive energy density ('The Solubility of Non Electrolytes', Hildebrand, J. H., Scott, R. L. (1950)), the solubility parameter, it is found that in general solvents having solubility parameters between 15 and 30 $J^{1/2}/cm^{3/2}$ are preferred for a PHA such as poly 3-hydroxybutyrate or poly 3-hydroxy-butyrate/poly 3-hydroxyvalerate copolymers.

PHA precipitated by the addition of water may be in the form of a gel. This may be compressed to expel solvent and/or water to leave flakes of PHA.

It is preferred that the vegetable matter should contain substantial quantities of PHA for example 10 to 60% by weight of PHA.

It is preferred that vegetable matter after treatment according to this invention be used as animal feed. It is preferred therefore that the solvents used in this invention should be acceptable in animal feed so that residues of the solvents may be tolerated in it. It is however preferred that substantially all of the solvent be removed from the vegetable residue

EXAMPLE 1

Spent rape seed meal (the residue left after conventional extraction methods for rape seed oil including cooking, crushing and hexane extraction)was mixed with poly 3-hydroxybutyrate polymer particles in a ratio of 2:1 weight of rape meal to polymer.

20 g of the mixture was suspended by agitation in 100 ml of hexanol solvent and heated to 140° C. The solution was maintained at 140° for 30 minutes then the rape meal solids filtered off by pressure filtration at 2 bar using a metal mesh filter cloth.

The polymer solution was cooled to 70° C. with agitation of the solution at which point the polymer formed a rigid opaque gel in the solvent. The polymer was recovered from the solvent phase by compressing the polymer gel between closely spaced rotating rollers producing flakes of polymer largely free of solvent. The expressed solvent could be reused in further extractions directly or after appropriate purification methods, i.e. evaporation.

The resulting polymer flakes were further freed by solvent by heating to 80° C. The resulting polymer flakes were solvent free and comprised polymer which was 99.7% pure and of molecular weight 650,000.

EXAMPLE 2

Transgenic Arabidopsis thaliana containing 15% polyhydroxybutyric acid as described by Poirier et al. Bio/Technology (1995) 13 142–150 may be treated as follows:

Suspend by agitation 20 g of the dried material in 100 ml of isopropanol and heat in a pressurised vessel to 140° C. for 30 minutes to dissolve the poly 3-hydroxy-butyric acid. After polymer dissolution remove the solids from the liquid by filtration of the solution. (Maintain the filtered solution of poly 3-hydroxybutyrate in isopropanol under pressure to prevent evaporation of the solvent). Recover polymer from the solvent by adding at least 30 ml of water or by reducing the solution temperature to 30 to 60° C. and separate the solid poly-hydroxybutyric acid by filtering or centrifuging.

I claim:

1. A process in which a polymer or copolymer of hydroxyalkanoic acid (PHA) is recovered from matter derived from living organisms by dissolving the PHA at a temperature above 100° C. in a solvent which is a lower ketone, dialkyl ether or a lower monoalcohol or a monocarboxylic acid ester thereof, separating the solution from such matter and recovering PHA from the solution.

2. A process as claimed in claim 1 in which the solvent is a lower ketone, dialkyl ether or a lower alcohol.

3. A process as claimed in claim 2 in which the solvent has 1 to 10 carbon atoms.

4. A process as claimed in claim 1 in which the solvent is an ester having from 1 to 12 carbon atoms.

5. A process as claimed in claim 1 in which the matter derived from living organisms is derived from microorganisms or plants.

6. A process as claimed in claim 5 in which the matter is derived from oil bearing plant matter by extracting the oil and crushing and/or milling it.

7. A process as claimed in claim 6 in which the oil extraction is accomplished at least in part by dissolving the oil in a water immiscible solvent in which the PHA is substantially insoluble.

8. A process as claimed in claim 1 in which the PHA is a polymer or copolymer of hydroxybutyric acid.

9. A process as claimed in claim 1 in which PHA is dissolved at a temperature in the range 100 to 150° C. and is recovered by cooling the solution to a temperature in the range 20 to 80° C. or, if the solvent is water miscible, cooling to a temperature of at most 100° C. and adding water.

10. A process as claimed in claim 1, 5, or 6 in which plant matter remaining after the extraction of PHA and reduction of its solvent content is fed to animals.

11. A process as claimed in claim 4, wherein the ester has from 4 to 10 carbon atoms.

12. A process as claimed in claim 9, wherein the solution is cooled to a temperature from 30 to 50° C., or if the solvent is water miscible, to a temperature of 20 to 90° C.

* * * * *